US005132220A

United States Patent [19]

Shapiro et al.

[11] Patent Number: 5,132,220

[45] Date of Patent: Jul. 21, 1992

[54] MORE VIRULENT BIOTYPE ISOLATED FROM WILD-TYPE VIRUS

[75] Inventors: Martin Shapiro, Columbia; Dwight E. Lynn, Severn; Edward M. Dougherty, Fulton, all of Md.

[73] Assignee: The United States of America as represented by the Secretary of Agriculture, Washington, D.C.

[21] Appl. No.: 373,977

[22] Filed: Jun. 30, 1989

[51] Int. Cl.$^5$ .............................. C12N 7/00

[52] U.S. Cl. .............................. 435/235.1; 435/5; 424/93 T

[58] Field of Search .............................. 435/5, 235.1; 424/93

[56] References Cited

U.S. PATENT DOCUMENTS

| | | | |
|---|---|---|---|
| 4,337,314 | 6/1982 | Oeschger et al. | 435/252.3 |
| 4,514,497 | 4/1985 | Kit et al. | 435/235.1 |
| 4,535,060 | 8/1985 | Comai | 435/240.2 |
| 4,870,023 | 9/1989 | Fraser et al. | 435/320 |

OTHER PUBLICATIONS

Martin Shapiro et al., "Comparative Infectivities of Gypsy Moth (Lepidoptera: Lumantriidae) Nucleopolyhedrosis Virus Isolates from North America, Europe, and Asia," J. Econ. Entomol. 77: 153-156 (1984).

Martin Shapiro and Edward Dougherty, "Selection of Active Strains of the Gypsy Moth Nuclearpolyhedrosis Virus," Proc. Symp.: Microbial Control of Spruce Budworm and Gypsy Moths, GTR-NE-100, pp. 115-122 (1985).

Martin Shapiro, "In vivo Selection of More Virulent Biotypes of the Gypsy Moth NPV," Soc. Invertebr. Pathol. XX Annu. Mtg. Abstr. 92, p. 85, Jul. 20-24 (1987).

*Primary Examiner*—Esther L. Kepplinger
*Assistant Examiner*—Donna C. Wortman
*Attorney, Agent, or Firm*—M. Howard Silverstein; John D. Fado; Joseph A. Lipovsky

[57] ABSTRACT

A method has been found to select the most virulent biotypes from a wild-type entomopathogenic virus by selection of desirable characteristics after serial passages through in vivo and in vitro systems. Using this method, a strain of *Lymantria dispar* NPV virus was isolated which had increased biological activity and increased speed of kill.

1 Claim, No Drawings

MORE VIRULENT BIOTYPE ISOLATED FROM WILD-TYPE VIRUS

BACKGROUND OF THE INVENTION

1. Field of the Invention

This invention relates to a method of selecting the most virulent biotypes from wild-type entomopathogenic viruses and the novel strains of viruses isolated thereby.

2. Description of the Prior Art

One of the impediments to the use of viruses against insect pests is that entomopathogenic viruses act relatively slowly, usually requiring several days or more to cause a lethal infection. Larvae continue to feed until shortly before death; therefore, field applications may not provide adequate crop or foliage protection.

For example, the gypsy moth, *Lymantria dispar* (L.), is an important forest pest in North America, Europe, and Asia and may cause widespread defoliation. The gypsy moth was responsible for defoliating over 5 million acres (ca. 2.0 million ha) in North America during 1980, over 12 million acres (ca. 4.9 million ha) in 1981, and over 8 million acres (ca. 3.2 million ha) during 1982. Under natural conditions, a nucleopolyhedrosis virus (NPV) is an important mortality factor and may cause population collapse [Glaser, J. Agric. Res. 4: 101-128 (1915); Vasiljevic, Trans. I Int. Congr. Insect Pathol. Biol. Control, Praha, pp. 215-216 (1958); Podgwaite, U.S. Dep. Agric. Handb. No. 539, 15 pp. (1979)]. The virus has been used as a control agent and was registered in the United States as Gypchek [Lewis et al., U.S. For. Serv. Res. Pap. NE-441, 9 pp. (1979a); Lewis et al., U.S. For. Serv. Res. Pap. NE-447, 8 pp. (1979b)].

Although NPV was successfully used to reduce gypsy moth populations [Rollinson et al., J. Invertebr. Pathol. 7: 515-517 (1965); Injac and Vasiljevic, Plant Prot. 29, No. 143-144: 43-56 (1978); Lewis et al., supra (1979b)], the virus is relatively slow acting, and larvae may continue to feed for almost 2 weeks after exposure. Greater foliage protection and population could occur if viral activity could be increased, either by selection of more desirable isolates [Shapiro and Ignoffo, J. Invertebr. Pathol. 16: 107-111 (1970)] or by the addition of adjuvants [Doane and Wallis, J. Insect. Pathol. 6: 423-429 (1964); Yadava, Z. Angew. Entomol. 65: 175-183 (1970); Shapiro and Bell, Ann. Entomol. Soc. Am. 75: 346-349 (1982)].

Differences in biological activity can be detected among geographical "races" of the same NPV species [Ossowski, J. Insect. Pathol. 2: 35-43 (1960); Smirnoff, J. Insect Pathol. 3: 29-46 (1961); Chauthani et al., J. Invertebr. Pathol. 12: 335-338 (1968); Shapiro and Ignoffo, supra], including the gypsy moth NPV [Magnoler, Entomophaga 15: 407-412 (1970); Rollinson and Lewis, Plant Prot. 24, No. 124-125: 163-168 (1973); Vasiljevic and Injac, Plant Prot. 24, No. 124-125: 169-186 (1973)].

Shapiro et al. [J. Econ. Entomol. 77: 153 (1984)] found that NPV isolated from different geographical locations differed as much as 3000-fold in activity. When these isolates were passed serially four times through *L. dispar* larvae, the activity of some isolates increased significantly during the second passage. In general, the activities became stabilized from the second to the fourth passage and became similar to the activity of the standard.

Previous studies also reported increases in the biological activities of insect viruses during serial passage [Veber, Colloq. Int. Pathol. Insectes, Paris 3: 403-405 (1962); Smirnoff, J. Insect Pathol. 5: 104-110 (1963); Woodward and Chapman, J. Invertebr. Pathol. 11: 296-301 (1968); Shapiro and Ignoffo, supra]. In the latter case, the pathogenicity of a *Baculovirus heliothis* isolate increased after five serial passages, and remained unchanged during 11 subsequent passages [Shapiro and Ignoffo, supra]. Serial passage is thought to select a more active isolate from a heterogeneous population, resulting in a more stable, homogeneous virus population [Veber, supra; Shapiro and Ignoffo, supra].

Genotypic variants in wild-type isolates of baculovirus populations are easily recognized by the presence of submolar fragments in the electrophoretic patterns of restriction endonuclease (REN) digestion products. There is a variation in bands of restriction fragments among various geographical isolates, showing both intra-strain and inter-strain heterogeneity among *Lymantria dispar* NPVs. Moreover, even within different plaque purified isolates of *L. dispar* NPV, at least five groups could be identified based upon the profile of REN digests. Comparison of the five groupings of plaque isolates having common patterns and virulence show that genotypic variants of *L. dispar* NPV display differential virulence. These studies have shown that there is a diversity of genomic material within a given wild-type virus [Shapiro and Dougherty, Proc. Symp.: Microbial Control of Spruce Budworms and Gypsy Moths, p. 115 (1985)].

SUMMARY OF THE INVENTION

We have now discovered that the most virulent biotypes of entomopathogenic viruses may be isolated by selection of multiple desirable characteristics and a combination of serial passages through in vivo and in vitro systems.

It is an object of this invention to teach a method to select the most virulent virus from a wild-type mixture of viruses.

It is a further object of this invention to provide a new NPV virus which possesses both quick kill and high activity toward *L. dispar* larvae.

Other objects and advantages of this invention will be readily apparent from the ensuing description.

DETAILED DESCRIPTION OF THE INVENTION

In the treatment of insect populations with viral pathogens, a number of properties are necessary for a useful virus. For example, both quick kill and high virulence are required for a successful viral pathogen. We have discovered that viral strains having the desired properties may be isolated from wild mixed viral strains by combining in vivo and in vitro serial passages and selection procedures.

Our method comprises the following steps:

(a) selecting an appropriate sample of wild virus;
(b) dividing the virus into multiple subsamples;
(c) screening each subsample against a susceptible insect species for the desired characteristics;
(d) ranking the series of samples from highest to lowest activity for each characteristic;
(e) selecting the sample which has the best combined characteristics;
(f) propagating the virus selected in (e);

(g) using the virus propagated in (f) and repeating steps (b) through (f) multiple times until stability in the desired characteristics is attained;

(h) collecting hemolymph from insects infected with virus obtained in step (g);

(i) infecting IPLB-LdFB [Lynn et al., In Invertebrate and Fish Tissue Culture, pp. 239-242, Japan Scientific Societies Press, Tokyo (1988)] cells with filtrate from infected hemolyph;

(j) culturing the viral infected cells;

(k) adding supernatant from (j) to IPLB-LdEIt [Lynn et al., supra] cells;

(l) removing plaque from the cells in (k), re-infecting and culturing IPLB-LdFB cells;

(m) selecting the best clones by counting occulusion bodies;

(n) repeating steps (i) through (m) multiple times until stability in the desired characteristics is obtained.

The above procedure will be effective if there exists within the original wild-virus a strain which combines the desired characteristics.

In a preferred example using this procedure, a strain of *L. dispar* NPV virus was isolated from a wild strain of Abington NPV. After ten passages through gypsy moth larvae, both the speed of kill and overall activity of the virus were increased substantially.

The Abington NPV isolate was divided into 20 subsamples. Each subsample was bioassayed at concentrations ranging from $5\times10^2$PIB/ml to $5\times10^6$PIB/ml against late second-instar gypsy moth larvae. Mortality for each virus subsample was recorded at day 7 for early kill at the 3 highest doses and at day 21 for total activity (=LC50).

Each subsample was ranked for both early kill and LC50, with 1=best activity and 20=worst activity (Table I). The best combination of early kill plus total activity was utilized as inoculum for the next passage. A correlation was then made between early kill and total activity to determine whether a relationship exists between the two selectable activities. From the data it should be noted that isolate 1 (rank 1 for early kill, rank 3 for total activity) would be selected as inoculum for the next passage. At every passage a standard virus (LDP-67; Hamden, Conn.) was also tested and passed, and differences between the Abington, Mass. selected isolate and the standard (Hamden, Conn.) are recorded.

The activity of Abington relative to that of Hamden serves as the basis for determination of changes in total activity during in vivo selection.

After ten passages through gypsy moth larvae, the speed of kill of the selected Abington isolate had been increased, and a greater percentage of the selected NPV population exhibited the faster kill. At the initial passage, the Abington geographical isolate not only killed gypsy moths faster than the standard Hamden isolate but also had greater total activity. As the number of selection steps proceeded, the Abington NPV continued to improve, i.e., more host larvae were killed sooner (Table II). Total activity did not increase during the first seven passes. At the eighth passage, however, the selected Ab biotype not only killed gypsy moth larvae sooner, but the relative total activity increased. After ten passes, the selected Ab biotype was ca. 10-fold more active than the standard Hamden isolate (Table III).

TABLE I

Biological Activity of the Abington, MA Geographical Isolate of *Lymatria dispar* NPV

| Kill at Day 7[a] | Rank | LC50[b] | Rank |
|---|---|---|---|
| 30 | 1 | 3.0 | 3 |
| 29 | 2 | 8.5 | 15 |
| 28 | 3 | 26.0 | 20 |
| 26 | 4 | 1.6 | 2 |
| 25 | 5 | 3.7 | 5 |
| 23 | 6 | 4.5 | 6 |
| 21 | 7 | 25.0 | 19 |
| 16 | 8 | 7.6 | 14 |
| 15 | 9 | 5.0 | 8 |
| 14 | 10 | 4.5 | 7 |
| 14 | 11 | 9.2 | 16 |
| 13 | 12 | 0.96 | 1 |
| 13 | 13 | 7.4 | 11 |
| 8 | 14 | 14.0 | 18 |
| 8 | 15 | 5.0 | 10 |
| 6 | 16 | 7.4 | 12 |
| 4 | 17 | 9.5 | 17 |
| 3 | 18 | 3.5 | 4 |
| 1 | 19 | 5.0 | 9 |
| 1 | 20 | 7.5 | 13 |
| x = 14.95 ± 9.62 | | x = 7.94 ± 6.56 | |

[a]Number of dead/90 larvae
[b]PIB/ml × $10^3$; mortality at day 21

TABLE II

Selection for More Virulent Biotypes of the Abington Isolate: Early Kill

| | Passage | | | | | | | | | |
|---|---|---|---|---|---|---|---|---|---|---|
| Kill at Day 7[a] | 1 | 2 | 3 | 4 | 5 | 6 | 7 | 8 | 9 | 10 |
| LDP-67 (standard) | 2 | 0 | 7 | 4 | 7 | 1 | 9 | 9 | 9 | 9 |
| Ab (selected) | 11 | 16 | 20 | 22 | 25 | 21 | 33 | 34 | 35 | 33 |

[a]Average number of dead/90 larvae

In addition, a greater percentage of the selected Ab population exhibited the faster kill (Table IV). At the first passage, only 5% of the Ab NPV was capable of killing >20/90 test larvae at day 7. At the third passage, 25% of the virus population exhibited the faster kill; at the seventh passage, 100% of the virus population exhibited the faster kill. Initially, the Ab isolate killed ca. 11/90 larvae at day 7. As selection progressed, the selected Ab biotype killed greater numbers of larvae by day 7, reaching a peak of ca. 33-35/90 larvae at pass 7 (Table II). As selection has proceeded, the correlation between early kill and total activity has also increased (Table V), so that a greater percentage of the selected virus population not only acts rapidly but also has good activity. In summary, selection of two desirable traits (i.e., speed of kill and total activity) has resulted in a more homogeneous, active NPV population.

The selected strain of Ab NPV was then subject to in vitro cloning procedures.

Hemolymph was collected from fourth and fifth instar larvae which had been infected by feeding occulusion bodies from the in vivo isolate and filtered to produce filtered virus inocula.

IPLB-LdFB cells were infected with the filtered virus inocula and cultured for 10 days. Supernatant from this culture was added to IPLB-LbEIt cells. After culturing 12 days, viral plaques were removed and reinoculated with IPLB-LdFB cells.

After 7 to 9 days the IPLB-LdFB cells were evaluated by counting occlusion bodies, and the best clones were selected. Occlusion bodies from the selected clones were used to inoculate larvae, and the procedure was repeated. A triple clone Abington virus designated Ld MNPV-Ab-a624 was thus obtained.

TABLE III

| Selection for More Virulent Biotypes of the Abington Isolate: Total Activity | | | | | | | | | |
|---|---|---|---|---|---|---|---|---|---|
| Passage[a] | | | | | | | | | |
| 1 | 2 | 3 | 4 | 5 | 6 | 7 | 8 | 9 | 10 |
| 4.9 | 2.2 | 2.8 | 2.6 | 3.2 | 3.4 | 4.1 | 11.1 | 6.6 | 11.9 |

[a]Ratios of LC50s of LDP-67 (standard) and Ab (selected), where activity of LDP-67 = 1.00, mortality at day 21.

TABLE IV

Selection for More Virulent Biotypes of the Abington Isolate: Virus Population Profile[a]

| Number of Larvae Dead | Passage 1 | 3 | 5 | 7 | 9 |
|---|---|---|---|---|---|
| 0-5 | 10% | 5% | | | |
| 6-10 | 55% | 5% | | | |
| 11-15 | 30% | 20% | | | |
| 16-20 | 5% | 40% | 20% | | |
| 21-25 | 5% | 10% | 40% | 20% | 30% |
| 26-30 | | 10% | 20% | 10% | — |
| 31-35 | | 5% | 10% | 40% | 30% |
| 36-40 | | — | 10% | 20% | 10% |
| 41-45 | | 5% | | — | 20% |
| 46-50 | | | | 10% | — |
| 51-55 | | | | | — |
| 56-60 | | | | | — |
| 61-65 | | | | | 10% |

[a]Percent of virus population specific larval mortality levels, number of larvae dead/90 larvae.

TABLE V

Correlation Between Early Kill and Total Activity of Selected Ab

| Passage | Correlation Coefficient (r =) |
|---|---|
| 1 | −0.058 |
| 2 | +0.017 |
| 3 | +0.184 |
| 4 | +0.612 |
| 5 | +0.576 |
| 6 | +0.709 |
| 7 | +0.745 |
| 8 | +0.770 |
| 9 | +0.794 |
| 10 | +0.804 |

The Ab NPV isolate Ld MNPV-Ab-a624 described above has been deposited with the American Type Culture Collection, Rockville, Md., under the conditions of the Budapest Treaty. It has been assigned the number ATCC VR2243.

As a practical matter, it is envisioned that commercial formulations of the subject viral pesticidal agent would be prepared directly from culture media such as larval homogenates or fractions derived from such homogenates, or cell cultures, thereby obviating the need to isolate the virus in pure form. Other suitable means could be readily determined by the skilled artisan. Of course, for applications demanding a high degree of specificity, i.e., a high level of predictability of the intended response by both target and nontarget organisms, it would normally be preferred to prepare the formulations from pure or substantially pure virus. For example, it is possible that extraneous substances in the larval material would have an undesirable effect in regard to the intended activity. The potency of ATCC No. VR2243 dictates that it be applied in conjunction with a suitable carrier or vehicle as known in the art. Of particular interest are those which are agronomically acceptable. Inert solids such as cellulose or sugars, wettable powders, and aqueous surfactant mixtures are illustrative of suitable chemical carriers. Depending on the substrate, target species, mode of application, and type of response desired, the concentration of virus in the final composition may vary considerably, but typically should be at least about $5\times10^{11}$ to $5\times10^{12}$ occlusion bodies per acre. Factors such as phytotoxicity toward the treated plant and tolerance of nontarget species can be used by the skilled artisan in determining the maximum level.

In the case of insect pathogens such as viruses, it is desirable to use biological carriers to distribute the pathogen. Such a biological carrier may be, for example, a species of insect which is closely related to the target species, but which is itself relatively unaffected by the pathogen. In this disclosure the word "carrier" is defined to include both chemical and biological carriers.

The level of virus is administered in an amount effective to induce infection as predetermined by routine testing. Where the ultimate response is pest mortality, an "effective amount" or "pesticidally effective amount" is defined to means those quantities of virus which will result in a significant mortality rate of a test group as compared to an untreated group. The actual effective amount may vary with the species of pest, stage of larval development, nature of the substrate, type of vehicle or carrier, period of treatment, and other related factors.

To be effective, the virus must be ingested by the insect; therefore, the virus must be applied to the locus of, or the vicinity of, the pest to be controlled. In the case of plants, the virus will typically be applied to the leaf surfaces.

The viral pesticide encompassed herein is effective in controlling a variety of insects. Without desiring to be limited thereto, pests of particular interest known to be vulnerable to treatment are agronomically important insects, especially those of the order Lepidoptera and more especially gypsy moth larvae.

The following examples are intended only to further illustrate the invention and are not intended to limit the scope of the invention which is defined by the claims.

EXAMPLE 1

Insects and Virus Inocula

The New Jersey-colonized strain of *L. dispar* (USDA-APHIS, Otis ANGB, MA) was used throughout the study. A wheat germ diet [Bell et al., U.S. Dep. Agric. Tech. Bull. 1584, 757 pp. (1981)] was used as the rearing medium (90 ml diet per 180-ml rearing container; Sweetheart Plastics, Wilmington, MA). The Abington, MA NPV isolate was obtained from virus-killed field-collected larvae and was compared to a Connecticut standard (LDP-67) in standardized bioassays [Shapiro and Bell, Ann. Entomol. Soc. Am. 74: 27-28 (1981)]. The Connecticut isolate was obtained in 1979 from the U.S. Forest Service (Hamden, CT) and has been used for both research and in vivo production (Shapiro et al., U.S. Dep Agric. Tech. Bull. 1584, 757 pp (1981)].

EXAMPLE 2

Selection and Passage

For each passage, the Abington NPV isolate was divided into 20 population samples and each sample was bioassayed. NPV was diluted in distilled water and was applied to the surface of the diet at concentrations of $5\times10^2$, $5\times10^3$, $5\times10^4$, $5\times10^5$, and $5\times10^6$ PIB per ml per cup ($=0.1\times10^0$ to $1.0\times10^3$ PIB per $mm^2$ of diet surface). Second instars (7 days old; avg. wt. =25 mg) were placed in each container (10 per cup) and were reared for 21 days at 29° Cm 50% RH, and a photoperiod of 12:12 CL:D). Thirty larvae were utilized per sample per virus dilution per passage (total =150 larvae per sample; 3000 larvae per passage) and 30 control larvae per passage.

Mortality for each virus sample was recorded at day 7 for early kill at the three highest concentrations ($=5\times10^4$, $5\times10^5$, $5\times10^6$ PIB/ml) and at day 21 for total activity (=LC50). Each sample was ranked for both early kill and LC50, with 1=best activity and 20 =worst activity. The sample exhibiting the best combination of early kill plus total activity was selected as inoculum for the next passage. At every passage, a standard virus (LDP-67) was also tested and passed. At the end of a passage (day 21), all larvae were collected, virus was extracted [Shapiro et al., supra], and a subsequent passage was made using the same virus concentrations.

EXAMPLE 3

Statistical Methods

At day 7, virus-caused mortality was recorded for larvae exposed to those concentrations which caused mortality (i.e., $5\times10^6$, $5\times10^5$, and rarely $5\times10^4$ PIB/ml) of the Abington isolate, as well as the CT standard. Concentration-mortality data were analyzed by ANDVA and LC50s (Ab vs LDP-67) were separated by Duncan's [Biometrics 11: 1-42 (1955)]multiple range test (P=0.05), but the activity of Abington relative to that of the CT standard served as the basis for determination of changes in total activity during in vivo selection.

For each passage,each abington population sample was ranked for both early kill (day 7) and LC50 (day 21), where 1=best and 20=worst. The sample exhibiting the best combination of early kill plus total activity was utilized as inoculum for the next passage. A correlation was made among Abington samples, in a given passage, between early kill and total activity (Steel and Tororie, need reference (1960)]. The simple regreesion analysis was utilized to determine the relationship between two attributes of viral activity (i.e., early kill, total activity) in a wild-type virus population, and whether changes would occur during purposefull selection. At the end of a passage (day 21), all larvae were collected, virus was extracted (Shapiro et at., supra], and a succeeding passage was made of both Abington and the CT standard, using the same virus concentrations.

EXAMPLE 4

Hemolymph Collection

Fourth and fifth instar *L. dispar* larvae infected by feeding occlusion bodies were surface sterilized with 70% ethanol on ice for 10 min. Larvae were blotted dry on paper towels and placed in a petri dish on crushed ice.

A proleg was cut with micro-scissors and the hemolymph was collected in 1.0 ml tissue culture medium (modified IPL-52B) containing 0.8 mg glutathione/ml on ice. The medium plus hemolymph was centrifuged 10 min (setting 3 on IEC Clinical centrifuge model CL) and the supernatant was filtered through a 0.45 μm filter (Uniflo) [=filtered virus inocula].

EXAMPLE 5

Cloning

IPLB-LdFB cells were centrifuged (setting 2, 5 min). The cell pellet was suspended 0.5 ml filtered virus inocula for 15 min. The cells were centrifuged (setting 2, 5 min), resuspended in 2 ml tissue culture medium (modified BML-TC/10 ), recentrifuged (setting 2, 5 min), resuspended in 4 ml modified BML-TC/10, and incubated at 27° C. After 10 days cultures were refrigerated (4° C.).

IPLB-LdEIT cells were seeded at $7.5\times10^5$ cells per well in 24-well Falcon tissue culture plate and incubated 4 hr at 27° C. for attachment. Supernatant from the IPLB-LdFB infected culture was serially diluted to $10^{-6}$. Of each dilution, 0.1 ml ($10^{-3}$ through 10hu −6) was added per well of IPLB-LdEIT plate. After 1 hr, the virus dilution was removed and 1 ml of 1.3% methylcellulose in BML/TC-10 was added per well.

After 12 days, plaques were removed with micro pipet tips and inoculated into 24-well plate containing IPLB-IdFB cells.

EXAMPLE 6

Evaluation of Clones

After 7 to 9 days, cells from clone-infected wells were collected and centrifuged (3 min, microfuge). The supernatant was collected and assayed by endpoint in IPLB-LdFB. IPLB-LdFB cells ($7.5\times10^5$ cells/well) were inoculated with 60 μm of the supernatant (4 wells with each virus clone) and incubated at 27° C.

After 7 days, the medium was removed from each well without distrubing the cells, and 0.5 ml of sterile distilled water was added per well. Cells were suspended in the water and 55 μl of 10% SDS was added to each well.

After thee occlusion bodies had settled, the numberr in each well was determined by counting 5410 $\mu m^2$ with a Leitz inverted microscope. Occlusion bodies from IPLB-LdFB cells infected with the best 3 or 4 clones were fed to 2-day-old and 2-week-old gypsy moth larvae.

EXAMPLE 7

Recloning

Examples 4, 5, and 6 were repeated once with hemolpmph from larvae fed coloned virus and a second time with larvae fed virus from subclones to arrive at triple clone Abington virus designated LdMNPV-Ab-a624.

It is understood that the foregoing detailed description is given mainly by way of illustration and the modification and variation may be made therein without departing from the spirit and scope of the invention.

We claim:

1. A biologically pure culture of an entomopathogenic viral strain having all the identifying characteristics of ATCC Accession No. VR 2243.

* * * * *